United States Patent [19]

Von Voigtlander

[11] Patent Number: 4,663,335

[45] Date of Patent: May 5, 1987

[54] TRANS-(+)-2-(3,4-DICHLOROPHENYL)-N-METHYL-N-[2-(1-PYRROLIDINYL)CYCLOHEXYL]ACETAMIDE, AND SALTS THEREOF AS CNS ANTI-SEIZURE DRUGS

[75] Inventor: Philip F. Von Voigtlander, Gunplain Township, Allegan County, Mich.

[73] Assignee: The Upjohn Company, Kalamazoo, Mich.

[21] Appl. No.: 791,314

[22] Filed: Oct. 25, 1985

[51] Int. Cl.$^4$ ............................................. A61U 31/41
[52] U.S. Cl. ................................................... 514/359
[58] Field of Search ....................................... 514/359

[56] References Cited

U.S. PATENT DOCUMENTS 4,098,904 7/1978 Szmuszkovicz ..................... 424/324
4,145,435 3/1979 Szmuszkovicz ..................... 424/274

OTHER PUBLICATIONS

F. C. Tortella et al, *Neuroscience Abstracts*, 10, p. 408, (Oct. 1984).
C. R. Randall et al, *J. Med. Chem.*, (1984), 27, pp. 779-782.
R. P. Simon et al, *Science*, 226, (Nov. 1984), pp. 850-852.
E. F. Berman et al, *Neuropharmacology*, 23, No. 3, pp. 367-371 (1984).
*The Merck Index*, 10th Edit. (1983), p. 1054, item 7204.

*Primary Examiner*—Stanley J. Friedman
*Attorney, Agent, or Firm*—John T. Reynolds

[57] ABSTRACT

The trans(+)-2-(3,4-dichlorophenyl)-N-methyl-N-[2-(1-pyrrolidinyl)cyclohexyl]acetamide enantiomer, and salts thereof, have been found to be useful as Central Nervous System anti-seizure drugs, at reasonable dosages in warm-blooded animal patients, including humans, as determined in a standard anti-convulsant laboratory animal tests.

3 Claims, No Drawings

TRANS-(+)-2-(3,4-DICHLOROPHENYL)-N-METHYL-N-[2-(1-PYRROLIDINYL)CYCLOHEXYL]ACETAMIDE, AND SALTS THEREOF AS CNS ANTI-SEIZURE DRUGS This invention relates to the use of certain N-[(2-aminocyclohexyl)benzacetamide compounds as drugs to prevent or block CNS seizures, e.g., convulsions, in warm-blooded animal patients, including humans. More particularly, this invention provides a process or method for treating CNS seizures in patients suffering from stroke, brain trauma, cardiovascular collapse and related brain and/or spinal damage.

BACKGROUND OF THE INVENTION

Szmuszkovicz U.S. Pat. No. 4,098,904 discloses some N-(2-aminocycloaliphatic)benzamide compounds, e.g., N-methyl-N-[2-(1-pyrrolidinyl)cyclohexyl]-3,4-dichlorobenzamide, and N-methyl-N-[2-(N',N'-dimethylamino)cyclohexyl]-4-bromobenzamide, and salts and hydrates thereof as analgesic (pain-reducing) drug compounds.

Szmuszkovicz U.S. Pat. No. 4,145,435 discloses some 2-aminocycloaliphatic amide compounds, e.g., N-methyl-N-[2-(N',N'-dimethylamino)cyclohexyl]-2-(4-bromophenyl)acetamide and trans-2-(3,4-dichlorophenyl)-N-methyl-N-[2-(1-pyrrolidinyl)cyclohexyl]acetamide, and their pharmaceutically acceptable salts as analgesic compounds.

The use object compound involved in this invention, trans(+)-2-(3,4-dichlorophenyl)-N-methyl-N-[2-(1-pyrrolidinyl)cyclohexyl]acetamide, and pharmaceutically acceptable salts thereof including the maleate salt, and methods for making such compounds are described in Example 34 of Szmuszkovicz U.S. Pat. No. 4,145,435. That '435 patent refers generally to the resolution of stereo isomers. That '435 patent also discloses that preliminary pharmacological testing of the separated trans-d- and trans-l-isomers of the compound, trans-2-(3,4-dichloro-phenyl)-N-methyl-N-[2-(1-pyrrolidinyl)cyclohexyl]acetamide maleate, indicated that the analgesic activity of those resolved isomers resides in the l-isomer, but analgesic activity was also shown by the trans-dl-isomer mixtures thereof.

In *Neuroscience Abstracts*, 10, page 408 (October, 1984), F. C. Tortella et al report the Seizure-specific, Dose- and Time-Dependent Anti-convulsant Profile of Upjohn compound, Trans-(±)-3,4-dichloro-N-methyl-N-[2-(1-pyrrolidinyl)cyclohexyl]-benzeneacetamide by an electroshock test method. This compound is described and claimed in the above Szmuszkovicz '435 patent. However, as indicated hereinabove this compound is an analgesically active compound.

Recent pharmacology articles that may be of interest as background are:

*J. Med. Chem.*, 1984, 27, pp. 779-782, "Anti-convulsant ... 4-Aminobenzamides" by C. Randall Clark et al,

*Science*, 226, Nov. 16, 1984, pp. 850-852, "Blockade . . . Against Ischemic Damage in the Brain" by R. P. Simon et al, and

*Neuropharmacology*, 23, No. 3, pp. 367-371 (1984), "The Anti-convulsant . . . Electroshock Seizures in Rats" by E. F. Berman et al, although these references are not conceded to be prior art to the invention described and claimed herein.

The compound trans-(+)-2-(3,4-dichlorophenyl)-N-methyl-N-[2-(1-pyrrolidinyl]benzeneacetamide and its maleate salt (U-53,445E) is disclosed in U.S. patent application Ser. No. 06/653,385 filed Sept. 21, 1984, as being the less active enantiomer of the racemic compound, trans-2-(3,4-dichlorophenyl)-N-methyl-N-[2-(1-pyrrolidinyl)cyclohexyl]acetamide for treating cerebral ischemia disorders, as determined by gerbil and Fischer rat laboratory animal tests.

OBJECTS AND SUMMARY OF THE INVENTION

It is an object of this invention to provide a method for preventing or treating CNS seizures, e.g., convulsions in warm-blooded valuable animal patients, including humans, while minimizing analgesic side effects of the drug in such patients by administering to such patient an effective amount of U-53,445, or a pharmaceutically acceptable salt thereof.

DETAILED DESCRIPTION OF THE INVENTION

Now, according to this invention, using a standard laboratory animal kainic acid antagonism test, it has been found that the trans(+)-enantiomer, that is, the trns(dextro-) or (R,R) stereo enantiomer of 2-(3,4-dichlorophenyl)-N-methyl-N-[2-(1-pyrrolidinyl)cyclohexyl]acetamide, and its salts have been found to have substantial CNS anti-seizure or anti-convulsant activity in useful dosage ranges, while having little if any analgesic side effect. The maleate salt of trans-(+)-2-(3,4-dichlorophenyl)-N-methyl-N-[2-(1-pyrrolidinyl)cyclohexyl]acetamide is referred to herein as U-53,445E.

According to the kainic acid test, the test compound is investigated for its ability to antagonize clonic forelimb convulsions induced in test mice animals individually by the excitatory amino acid agonist, kainic acid.

In this test, groups of six CF-1 strain mice, weighing from 18 to 20 grams, are dosed subcutaneously with a 0.9 percent aqueous saline suspension of the test compound, in this case, of U-53,445E, in a volume dose of 10 ml. per kilogram of animal body weight. Fifteen minutes later kainic acid (0.08 micrograms per mouse) is administered intracranically. The mice were immediately housed individually in observation cubicles and scored over the next 30 minutes for clonic seizures of the forelimbs (piano-playing convulsions). Test animals not displaying this behavior were considered to be protected from the seizures induced by the excitatory kainic acid and agonist.

In this kainic acid test, the compound U-53,445E had a calculated $ED_{50}$ value of 100 mg./kg. (subcutaneously). Further evidence of the anti-convulsant activity of U-53,445E is obtained from the ability of this compound to block seizures induced in mice by maximal (10 mA, 0.2 sec) electroshock. U-53,445E has an $ED_{50}$ of 22 mg./kg. in this electroshock test. We also know that this compound U-54,445E, is essentially inactive, having an $ED_{50}$ of greater than 500 mg./kg. in the standard hydrochloric acid writhing analgesic test. Based upon these data, we believe U-53,445E will be an effective CNS anti-convulsant or anti-seizure drug in valuable warm-blooded animals such as cats, dogs, horses and other commercially valuable animals as well as in humans, at doses approximating 1.0 to 10 mg./kg./dose of trans(+)-2-(3,4-dichlorophenyl)-N-methyl-N-[2-(1-pyrrolidinyl)cyclohexyl]acetamide or one of its pharmaceutically acceptable salts, per kilogram of animal body weight.

The invention also relates to use of this compound, trans(+)-2-(3,4-dichlorophenyl)-N-methyl-N-[2-(1-pyrrolidinyl)cyclohexyl]acetamide, or one of its pharmaceutically acceptable salts in a pharmaceutical composition containing this compound as an active CNS anti-seizure ingredient in a pharmaceutical carrier. The compositions are useful in pharmaceutical dosage unit forms of the Formula I compounds for systemic administration (oral, rectal and parenteral administration form) in therapy for treating and alleviating seizures in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars, or sodium chloride in isotonic concentrations. Carriers nd vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to 350 mg. of the essential active ingredient per dosage unit form, which as aforesaid may be in the form of a semi-solid, oral, or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to prevent or block a CNS seizure or convulsion in the patient within the aforesaid effective non-toxic range. Expressed otherwise, when used systemically, an amount of the essentially active ingredient is provided to a recipient within a range from about 0.1 mg./kg. to about 100 mg./kg. of body weight of the recipient.

Preferred dosages for most applications are 1 to 1.0 mg./kg. of body weight.

The useful pharmaceutical dosage unit forms of these compounds in pharmaceutical formulations in preferably adapted for systemic administration to obtain anti-convulsant or anti-seizure effects comprising an effective, non-toxic amount of trans(+)-2-(3,4-dichlorophenyl)-N-methyl-N-[2-(1-pyrrolidinyl)cyclohexyl]acetamide, or as its pharmacologically acceptable salt.

Further, the invention relates to methods of obtaining anti-convulsant effects in mammals, for example, human and valuable warm-blooded animals, such as dogs, cats, horses and other commercially valuable animals, by administering systemically to the mammals the aforesaid pharmaceutical dosage unit forms supplying an effective, non-toxic amount for anti-convulsant or anti-seizure effects. These compounds have an advantage, to a greater extent, of having little or no analgesia side effect in the patient, as shown by evaluation of representative compounds and those standard drug compounds in various pharmacological test procedures which measure relative degrees of analgesia and the herein desired anti-convulsant CNS effect of the test compounds in standard laboratory test animals.

EXAMPLE 1

One thousand tablets for oral use, each containing 40 mg. of trans(+)-2-(3,4-dichlorophenyl)-N-methyl-N-[2-(1-pyrrolidinyl)cyclohexyl]acetamide as the essential active ingredient are prepared from the following ingredients:

Essential active ingredient—40 gm.
Dicalcium phosphate—150 gm.
Methylcellulose, U.S.P. (15 cps.)—6.5 gm.
Talc—20 gm.
Calcium stearate—2.0 gm.

The essential active ingredient and dicalcium phosphate are mixed well, granulated with 7.5 percent aqueous solution of methylcellulose, passed through a No. 8 screen and dried carefully. The dried granules are passed through a No. 12 screen, mixed with the talc and stearate and compressed into tablets. These tablets are useful to prevent or block CNS seizures in adult humans at a does of 1 tablet one to four times a day as needed.

EXAMPLE 2

One thousand two-piece hard gelatin capsules for oral use, each capsule containing 20 mg. of trans(+)-N-methyl-N-[2-(N-pyrrolidinyl)cyclohexyl]-2-(3,4- dichlorophenyl)acetamide maleate as the essential active ingredient are prepared from the following ingredients:

Essential active ingredient—20 gm.
    Lactose, U.S.P.—100 gm.
    Starch, U.S.P.—10 gm.
    Talc, U.S.P.—5 gm.
    Calcium stearate—1 gm.

The finely powdered materials are mixed thoroughly, then filled into hard gelatin capsules of appropriate size.

One capsule four times a day is useful for the treatment to prevent or block CNS seizures in adult humans.

EXAMPLE 3

One-piece soft elastic capsules for oral use, each containing 100 mg. of U-53,445E hydrochloride as the essential active ingredient are prepared in the usual manner by first dispersing the powdered active material in sufficient corn oil to render the material capsulatable.

One capsule two times a day is useful in the treatment to prevent or block CNS seizures in said human patient.

EXAMPLE 4

One thousand suppositories, each weighing 2.5 gm. and containing 50 mg. of trans-(+)-2-(3,4-dichlorophenyl)-N-methyl-N-[2-(1-pyrrolidinyl)cyclohexyl]acetamide hydrochloride as the essential active ingredient, are prepared from the following ingredients:

Essential active ingredient—50 gm.
    Propylene glycol—165 gm.
    Polyethylene glycol 4000 q.s.—2,500 gm.

The essential active ingredient is added to the propylene glycol and the mixture stirred until uniformly dispersed. The PEG 4000 is melted and the propylene glycol dispersion added. The suspension is poured into molds and allowed to cool and solidify.

These suppositores are useful in the treatment of patients to prevent or block CNS seizures in said patients at a dose of one suppository rectally twice a day.

EXAMPLE 5

A sterile aqueous suspension suitable for intramuscular injection and containing in each milliliter 50 mg. of the Example 1 essential active ingredient is prepared from the following ingredients:

Essential active ingredient—5 gm.
    Polyethylene glycol 4000, U.S.P.—3 gm.
    Sodium chloride—0.9 gm.
    Polysorbate 80, U.S.P.—0.4 gm.
    Sodium metabisulfite—0.1 gm.
    Methylparaben, U.S.P.—0.18 gm.
    Propylparaben, U.S.P.—0.02 gm.
    Water for injection, q.s. to—100 ml.

The preceding sterile injectable is useful in the treatment of patients to prevent or block CNS convulsions in said patient at a dose of ½ to 2 ml.

EXAMPLE 6

An aqueous oral preparation containing in each teaspoonful (5 ml.) 80 mg. of trans(+)-2-(3,4-dichlorophenyl)-N-methyl-N-[2-(1-pyrrolidinyl)cyclohexyl]acetamide maleate as the essential active ingredient is prepared from the following ingredients:

Essential active ingredient—160 gm.
    Methylparaben, U.S.P.—7.5 gm.
    Propylparaben, U.S.P.—2.5 gm.
    Saccharin sodium—12.5 gm.
    Glycerine—3,000 ml.
    Tragacanth powder—10 gm.
    Orange oil flavor—10 gm.
    Orange II—7.5 gm.
    Deionized water, q.s. to—10,000 ml.

The foregoing aqueous preparation is useful in the treatment of adult humans at a dose of one teaspoonful four times a day to prevent or block CNS seizures.

EXAMPLE 7

One thousand tablets for oral administration, each containing 10 mg. of trans(+)-N-methyl-N-[2-(N-pyrrolidinyl)cyclohexyl]-2-(3,4-dichlorophenyl)acetamide as the essential active ingredient are prepared from the following ingredients:

Essential active ingredient, micronized—10 gm.
    Lactose—150 gm.
    Starch—15 gm.
    Magnesium stearate—1.5 gm.

The ingredients are thoroughly mixed and slugged. The slugs are broken down by forcing through a screen and the resulting granules are then compressed into tablets.

These tablets are useful in preventing or blocking CNS seizures in dogs at a dose of one to three tablets depending on the weight of the animal and its condition.

I claim:

1. A method for preventing or blocking CNS seizures or convulsions in a warm-blooded animal patient which comprises administering to said patient suffering from such a CNS disorder an effective amount of trans(+)-2-(3,4-dichlorophenyl)-N-methyl-N-[2-(1-pyrrolidinyl)-cyclohexyl]acetamide, or a pharmaceutically acceptable salt thereof.

2. A method as described in claim 1 wherein the compound administered to the patient is trans(+)-2-(3,4-dichlorophenyl)-N-methyl-N-[2-(1-pyrrolidinyl)-cyclohexyl]acetamide hydrochloride.

3. A method as described in claim 1 wherein the compound administered to the patient is trans-(+)-2-(3,4-dichlorophenyl)-N-methyl-N-[2-(1-pyrrolidinyl)-cyclohexyl]acetamide maleate.

* * * * *